United States Patent [19]

Kraus

[11] Patent Number: 4,528,703

[45] Date of Patent: Jul. 16, 1985

[54] PORTABLE URINAL

[76] Inventor: Richard J. Kraus, 923 Oakmont St., Philadelphia, Pa. 19111

[21] Appl. No.: 624,278

[22] Filed: Jun. 25, 1984

[51] Int. Cl.³ .................. A61G 9/00; A47K 11/12
[52] U.S. Cl. ................. 4/144.2; 4/144.3; 4/144.1; 604/329; 604/347; 604/350
[58] Field of Search ............ 4/144.1, 144.2, 144.3; 604/329, 347, 350; 128/295

[56] References Cited

U.S. PATENT DOCUMENTS

| 241,863 | 5/1881 | Hopkins | 604/347 |
|---|---|---|---|
| 2,544,341 | 3/1961 | McGraw | 4/144.3 X |
| 2,968,046 | 1/1961 | Duke | 4/144.3 |
| 3,727,244 | 4/1973 | Collins | 4/144.3 |
| 4,023,216 | 5/1977 | Li | 4/144.3 |
| 4,187,562 | 2/1980 | Mioduski | 4/144.3 |
| 4,198,979 | 4/1980 | Cooney et al. | 604/329 |
| 4,202,057 | 5/1980 | Ibarra | 4/144.3 |
| 4,202,058 | 5/1980 | Anderson | 4/144.3 |
| 4,246,901 | 1/1981 | Michaud | 604/329 |
| 4,270,539 | 6/1981 | Michaud | 4/144.3 X |
| 4,305,161 | 12/1981 | Diaz | 4/144.2 |
| 4,421,511 | 12/1983 | Steer et al. | 4/144.3 X |

Primary Examiner—Henry K. Artis
Attorney, Agent, or Firm—Steele, Gould & Fried

[57] ABSTRACT

A portable urinal for women comprises: a rigid cup-shaped member for receiving urine, having an upward projection at one end and a spout extending from the opposite end for discharging urine in a directable stream, side walls therebetween having recessed portions; a flexible membrane covering the recessed portions of the side walls and having an upper body-sealing rim; and, at least two braces spaced from one another and extending between upper rims of the rigid recessed side walls. The projection is effective for positioning the urinal and enabling urine to enter the cup-shaped member without body obstruction. The flexible membrane is effective for preventing leakage during use and for wiping urine traces from the body after use. The braces are effective for preventing body contact with urine in the cup-shaped member during use. The portable urinal has a particularly flat, slim profile enabling use while standing and while substantially clothed.

20 Claims, 7 Drawing Figures

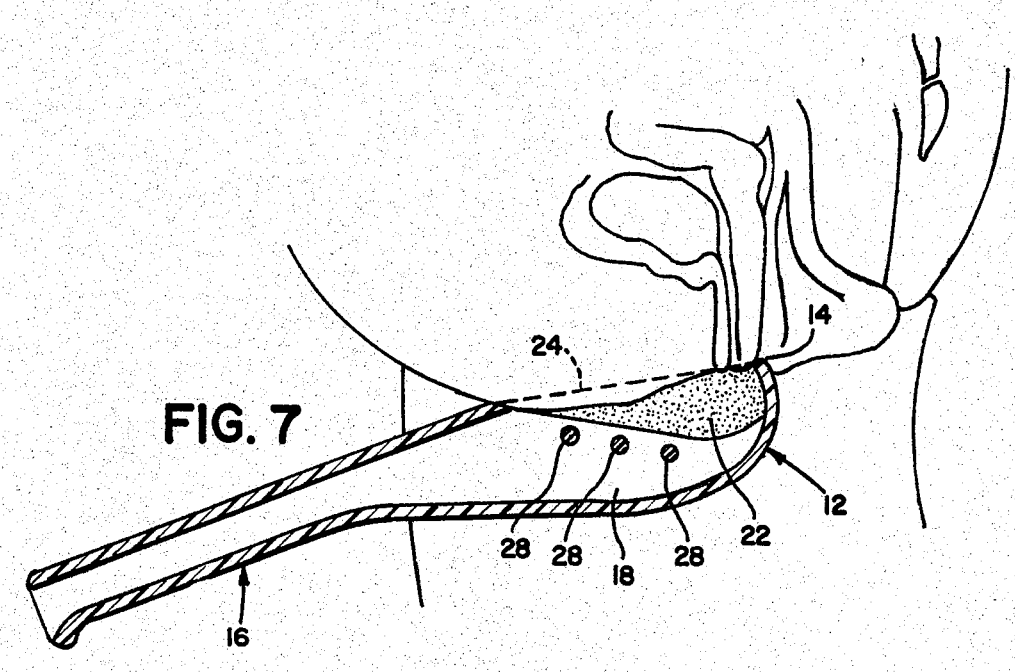
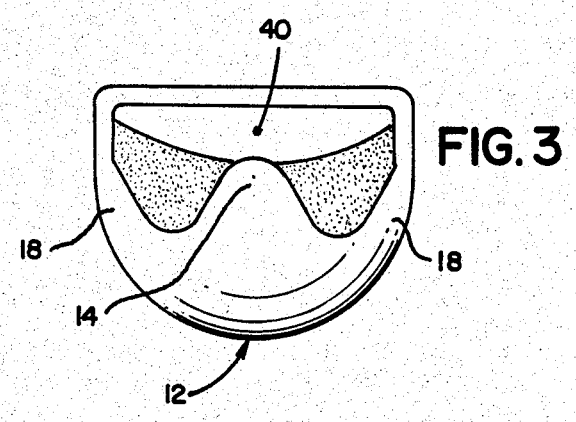
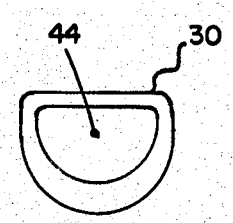

PORTABLE URINAL

BACKGROUND OF THE INVENTION

1. Field of the Invention

This invention relates to the field of portable urinals in general, and in particular, to portable urinals for women which can be used while standing and while substantially clothed.

2. Prior Art

Portable urinals have been known generally for some time, particularly as used for bedridden patients. The simplest form is of course the bedpan. Bedpans are awkward, and not entirely reliable, that is, not leakproof. An early alternative to such bedpans is disclosed in U.S. Pat. No. 241,863.

Portable urinals of a second sort are known, wherein urine is collected at a remote point. Examples of such urinals are disclosed in U.S. Pat. Nos. 4,202,057, 4,202,058, and 4,270,539.

A third kind of portable urinal are those designed to store the urine immediately adjacent the discharge, for disposal or testing at a more convenient location. Examples of this type of portable urinal are disclosed in U.S. Pat. Nos. 3,727,244, 4,187,562, and 4,305,161.

A final type of portable urinal for women is disclosed in U.S. Pat. No. 4,023,216. A rigid device of plastic or other suitable material gathers the poorly defined urinary efflux of a urinating human female in a normal standing position and directs it forwardly and downwardly in a defined stream to impinge on a chosen spot. The device comprises a trough open at the top and adapted to be positioned to register with the outlet of the urethra. There is a forwardly and downwardly inclined discharge conduit from the forward end of the trough. There is a replaceable absorbent pad at the rear of the trough to remove residual urine. Another embodiment, which is disposable, is made frmm foldable material such as paper with a waterproof lining.

The urinal disclosed in U.S. Pat. No. 4,023,216 is an improvement over the other noted references insofar as it is suitable for non-medical and non-hospital uses, and is convenient to use, at least with respect to prior art devices known at the time. However, such a device has several disadvantages. Firstly, it is relatively large and bulky, requiring substantial disrobing prior to use. Secondly, there are no reliable means included for positioning the device with reasonable precision. Thirdly, it is not entirely reliable with respect to being leakproof.

This invention overcomes all of the difficulties with portable urinals in general, and in particular, with those of the type disclosed in U.S. Pat. No. 4,203,216. Portable urinals for women according to this invention have means formed thereon for precisely positioning the urinal, have means for sealably engaging the body to prevent leaks during use, and are formed with a particularly slim and flat profile. In fact, portable urinals according to this invention can be used with no more disrobing than is ordinarily necessary for a male. Moreover, in view of the particularly flat profile, portable urinals according to this invention include structure preventing undesirable and uncomfortable body contact with urine in the urinal during use.

A most unique feature of portable urinals according to this invention lies in the projecting structure used in properly positioning the urinal for use. It will be appreciated that fashion dictates many women to wear tight-fitting clothing, for example, tight jeans. Most women's jeans are in fact provided with zippers at the front, as with men's trousers. It is frequently the case when wearing such fashions that the lips of the vagina will be tightly sealed and overlapped by hair. This makes it literally impossible to urinate into a small receptacle without spilling over, in the absence of undressing completely, at least below the waist. The portable urinal according to this invention is therefore provided with a projection just sufficient to be used to gently separate the lips of the vagina at the area of the urethra. The projection then serves as a means to positively and precisely position the urinal by gently pressing the projection against the forward rim of the vagina. The flexible membrane is not only effective for sealing the urinal to the body, and preventing leakage or backflow into the vagina, but together with the projection is effective for wiping urine traces from the body after use, as the urinal is removed.

Rigid plastic provides sufficient structural strength to withstand the stresses encountered when utilizing the device with tight-fitting garments as described above.

SUMMARY OF THE INVENTION

It is an object of this invention to provide an improved protable urinal for women which is safe and convenient to use wherever conventional toilet facilities are not available.

It is another object of this invention to provide an improved portable urinal for women which can be utilized without the need to undress.

It is still another object of this invention to provide an improved portable urinal for women which is sufficiently slim and flat in profile to facilitate its transportation and encourages its use.

These and other objects are accomplished by a portable urinal for women, ccmprising: a rigid cup-shaped member for receiving urine, having an upper projection at one end and a spout for discharging urine in a directable stream extending from the opposite end, side walls therebetween having recessed portions; and, a flexible membrane covering the recessed portions of the side walls and having an upper body-sealing rim, whereby the projection is effective for positioning the urinal and enabling urine to enter the cup-shaped member without body obstruction and the flexible membrane is effective for preventing leakage during use and for wiping urine traces from the body after use.

The portable urinal may further comprise at least two braces spaced from one another and extending between upper rims of the rigid recessed side walls, for preventing body contact with urine in the cup-shaped member during use. The spout defines a longitudinal axis, and has a substantially semi-circular cross-section throughout its length relative to the axis. The cup-shaped member has a longitudinal axis running between the ends of the cup-shaped member, the cup-shaped member also having a substantially semi-circular cross-section throughout its length. The free end of the projection and the rim of the flexible membrane lie in a common plane. The non-circular portion of the spout defines a flat peripheral wall portion, which in turn also defines a plane. The planes define an included angle which is in the range of approximately 165° to 175°, resulting in the particularly flat profile. The portable urinal may be manufactured from rigid and flexible plastics materials.

Other subjects and a fuller understanding of the invention will be had by referring to the following description and claims of a preferred embodiment thereof, taken in conjunction with the accompanying drawings, wherein like reference characters refer to similiar throughout the several views in which:

BRIEF DESCRIPTION OF THE DRAWINGS

Presently preferred embodiments of the invention are shown in the drawings for the purpose of illustrating the invention. It is to be understood, however, that this invention is not limited to the precise arrangements and instrumentalities shown.

FIG. 3 is a rear elevational view of the portable urinal shown in FIG. 1.

FIG. 5 is a front elevational view of the portable urinal shown in FIG. 1.

FIG. 7 illustrates the manner in which a portable urinal according to this invention may be used, the portable urinal being shown in longitudinal section.

DESCRIPTION OF THE PREFERRED EMBODIMENTS OF THE INVENTION

Figure 1:
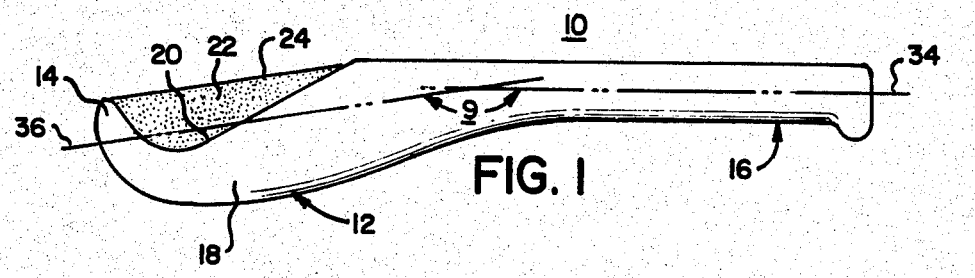
FIG. 1 is a side elevational view of a portable urinal according to this invention.
Figure 2:
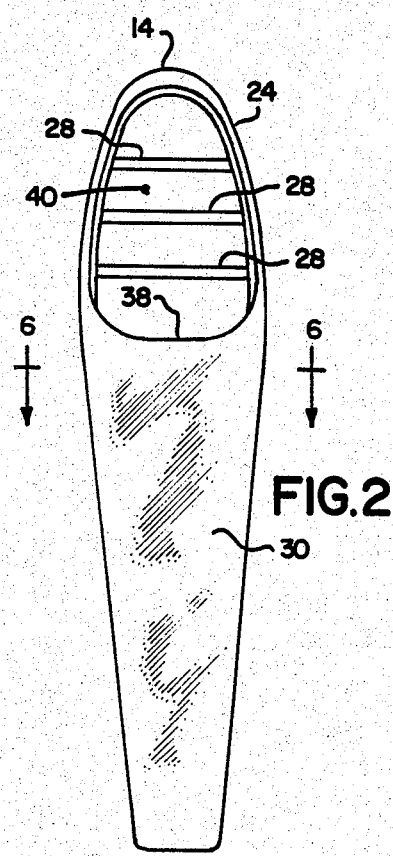
FIG. 2 is a top plan view, of the portable urinal shown in FIG. 1.
Figure 6:
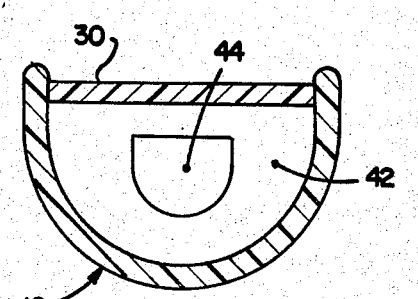
FIG. 6 is a section view taken along the line 6—6 in FIG. 2.

Although specific terms are used in the following description for the sake of clarity, these terms are intended to refer only to the particular structure of the invention selected for illustration in the drawings and are not intended to define or limit the scope of the invention.

A portable urinal 10 for women, according to this invention is illustrated in FIGS. 1-6. The portable urinal 10 comprises a cup-shaped member 12 for receiving urine, having an upward projection 14 at one end and a spout 16 extending from the opposite end, for discharging urine in a directable stream. Side walls 18 of the cup-shaped member between its opposite ends have recessed portions defined by curved or scallop-shaped upper side wall rims 20. A flexible membrane 22 covers the recessed or missing portions of the side walls 18 and has an upper body-engaging and body-sealing rim 24.

The uppermost tip of projection or point 14 and the upper rim 24 of the flexible membrane 22 define or lie in a common plane. An axis 36 for the cup-shaped member may be defined as running centrally through the cup-shaped member, parallel to the common plane. The cup-shaped member has a substantially semi-circular cross-section throught its length. A central axis 34 may be defined as running centrally through the bore defined by spout 16. The spout has a substantially semi-circular cross-section throughout its length, defining a flat peripheral wall portion 30. Axis 34 is parallel to the upper flat surface portion 30 of spout 16. The axes 34 and 36 of the spout and cup-shaped member, respectively, are disposed at an obtuse angle a relative to one another, the angle a being in the range of approximately 165°-175° in the presently preferred embodiment. In a similiar fashion, the plane defined by projection 14 and rim 24 is disposed at an identical angle to the plane defined by flat surface 30 of spout 16. However the angle is defined, it is such as results in a very flat profile in side elevation, as is apparent from FIG. 1.

Figure 4:
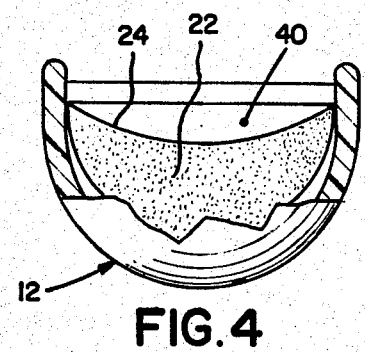
FIG. 4 is identical to FIG. 3, except that the end is broken away to fully show the flexible membrane.

The flexible membrane 22 may be conveniently formed by a single member as shown in FIG. 4, which is adhesively attached to the inner surface of the side walls 18 of the cup-shaped member by a liquid proof adhesive. The upper rim 24 of the flexible membrane 22 and an edge of flat portion 30 together define an opening 40 for receiving urine into the urinal. Urine travels through a transition area more or less in the vicinity of section line 6—6 in FIG. 2, which narrows from the large diameter of the cup-shaped member to the small diameter of the bore of spout 16. The transition area also has a substantially semi-circular cross-section. The urine flow is driven by the force of discharge and by gravity, and exits from aperture 44 in a sufficiently defined stream to be directed at a chosen spot.

Opening 40 is spanned by at least two, and preferably three braces 28 having two principle functions. One function is to provide additional structural rigidity to the entire device. This seoond feature relates to comfort during use. It has been determined that when the cup-shaped member is pressed against the body into an operative position, the fleshy part of the lips of the vagina tend to extend into the cup, which during urination, is likely to create a sensation of wetness. This sensation is likely, in turn, to cause unnecessary panic and embarrassment, as well as discomfort. Braces 28 prevent such contact between the body and urine in the cup-shapad member. The braces are preferably circular in cross-section in order to avoid sharp edges.

The cup-shaped member 12 and the spout 16 are preferrably made from any number of suitable rigid plastic materials. The urinal can be molded in one or more pieces and assembled as necessary. In view of the delicate function of the invention, it is of course important that the rigid materials be finished very carefully, so that it is as smooth as possible, with no sharp or jagged edges. The flexible membrane may also be made from a plastic material, any number being suitable, provided that they are sufficiently flexible to conform to body contour, yet sufficiently rigid when forming part of the overall structure to assure a good seal to prevent leaks. The flexible membrane can be welded to the rigid plastic material by solvent or thermal means.

Use of the portable urinal 10 is illustrated in FIG. 7. Such use can be best understood by considering instructions for use.

Firstly, the portable urinal must be positioned so that one can use the projection or point 14 to gently separate the lips of the vagina at the area of the urethra. Secondly, the point or projection 14 must be slid backwardly until the projection reaches the vagina. Thirdly, the urinal is moved forwardly until the projection just touches the forward rim of the vagina. Fourthly, firm upwardly directed pressure must be applied to assure sealing contact of the cup-shaped member with the body. Fifthly, the spout must be aimed slightly downwardly, so that the urine will flow therethrough and be discharged as required, without unduly accumulating within the device. Finally, the urinal is best removed with a gentle forward wiping motion so that urine traces can be removed from the body by the upper rim of the flexible membrane and the projection.

In order to provide a sense of scale and proportion, without being limiting, a portable urinal according to this invention will typically be approximately 7 inches long, and approximately 1⅜ inches laterally, at its widest point. The opening 40 is approximately 2¼ inches long.

The braces are approximately ⅛ of an inch in diameter and can be made of the same material as the shell.

A suitably strong and rigid structure will be formed if the plastic shell is frabricated approximately one-sixteenth of an inch in thickness. The shell may be made from wood or high density polyethylene plastic. The flexible membrane may be approximately 0.040 inches in thickness and may be fabricated from the product manufactured by General Electric Company under the trademark "AUTO SEAL". The membrane is preferably fabricated separately of the shell and can be affixed directly by employing small quantities of the "AUTO SEAL" product intermediate the parts.

It will be appreciated that this invention can be embodied in other specific forms without departing from spirit or essential attributes thereof. Accordingly, reference should be made to the appended claims, rather to the foregoing specification, as indicating the scope of the invention.

What is claimed is:

1. A portable urinal for women, comprising:
   a rigid cup-shaped member for receiving urine, having an upper projection at one end and a spout extending from the opposite end, for discharging urine in a directable stream; side walls between the ends having recessed portions; and,
   a flexible membrane covering the recessed portions of the side walls and having an upper body-sealing rim, whereby the projection is effective for positioning the urinal and enabling urine to enter the cup-shaped member without body obstruction and the flexible membrane is effective for preventing leakage during use and for wiping urine traces from the body after use.

2. A portable urinal according to claim 1, further comprising at least two braces spaced from one another and extending between upper rims of the rigid recessed side walls, for preventing body contact with urine in the cup-shaped member during use.

3. A portable urinal according to claim 2, comprising three of the braces.

4. A portable urinal according to claim 1 wherein, with respect to a longitudinal axis defined by the spout, the spout has a substantially semi-circular cross-section throughout its length.

5. A portable urinal according to claim 1 wherein, with respect to a longitudinal axis running between the ends of the cup-shaped member, the cup-shaped member has a substantially semi-circular cross-section throughout its length.

6. A portable urinal according to claim 5 wherein, with respect to a longitudinal axis defined by the spout, the spout has a substantially semi-circular cross-section throughout its length, defining a flat peripheral wall portion.

7. A portable urinal according to claim 6, wherein the free end of the projection and the rim of the flexible member lie in a common plane.

8. A portable urinal according to claim 7, wherein a plane defined by the flat portion of the spout lies at an obtuse angle relative to the plane of the flexible rim and the projection.

9. A portable urinal according to claim 8, wherein the obtuse angle is in the range of approximately 165° to 175°, whereby the urinal has a very flat profile.

10. A portable urinal according to claim 6, wherein the longitudinal axes define an included angle in the range of approximately 165° to 175°, whereby the urinal has a very flat profile.

11. A portable urinal according to claim 1, wherein the free end of the projection and the rim of the flexible membrane lie in a common plane.

12. A portable urinal according to claim 1, wherein the urinal is made from rigid and flexible plastic materials.

13. A portable urinal according to claim 1, having a substantially semi-circular cross-section throughout its length.

14. A portable urinal for women, comprising,
   an elongated rigid shell, having a cup-shaped portion for receiving urine and a spout for discharging urine from the cup-shaped portion in a directable stream, the cup-shaped portion having recessed side walls defining an upward projection opposite the spout; and,
   a flexible membrane covering the recessed portions of the side walls and having an upper body-sealing rim, whereby the projection is effective for positioning the urinal and enabling urine to enter the cup-shaped member without body obstruction and the flexible membrane is effective for preventing leakage during use and for wiping urine traces from the body after use.

15. A portable urinal according to claim 14, wherein the shell has a substantially semi-circular cross-section throughout its length.

16. A portable urinal according to claim 14, wherein the sidewall recesses are curved.

17. A portable urinal according to claim 14, wherein the projection and the rim of the membrane lie in a common plane.

18. A portable urinal according to claim 15, wherein the the sidewall recesses are curved.

19. A portable urinal according to claim 15, wherein the projection and the rim of the membrane lie in a ccmmon plane.

20. A portable urinal according to claim 18, wherein the projection and the rim at the membrane lie in a common plane.

* * * * *